(12) United States Patent
Pitkin et al.

(10) Patent No.: US 6,290,730 B1
(45) Date of Patent: Sep. 18, 2001

(54) ARTIFICIAL FOOT AND ANKLE (75) Inventors: Mark R. Pitkin, Sharon, MA (US); John A. Hays; Sujatha Srinivasan, both of Columbus, OH (US); James M. Colvin, Hilliard, OH (US)

(73) Assignee: Ohio Willow Wood Company, Mount Sterling, OH (US)

( * ) Notice: Subject to any disclaimer, the term of this patent is extended or adjusted under 35 U.S.C. 154(b) by 0 days.

(21) Appl. No.: 09/526,367

(22) Filed: Mar. 16, 2000

Related U.S. Application Data (60) Provisional application No. 60/126,348, filed on Mar. 26, 1999.

(51) Int. Cl.[7] .................................................. A61F 2/66
(52) U.S. Cl. ................................................. 623/49; 623/55
(58) Field of Search .................................. 623/55, 49, 51, 623/52, 50

(56) References Cited

U.S. PATENT DOCUMENTS

| 26,753 | 1/1860 | Douglass | 623/53 X |
|---|---|---|---|
| 197,943 | 12/1877 | Osborne | 623/53 X |
| 456,206 | 7/1891 | Rowley | 623/55 |
| 854,510 | 5/1907 | Mahaffey | 623/49 |
| 1,090,327 | 3/1914 | Milligan | 623/53 X |
| 1,219,374 * | 3/1917 | Carrico | 623/55 |
| 5,019,109 * | 5/1991 | Voisin | 623/55 |
| 5,062,859 | 11/1991 | Naeder | 623/55 |
| 5,139,525 | 8/1992 | Kristinsson | 623/55 |
| 5,156,632 | 10/1992 | Wellershaus | 623/55 |
| 5,376,139 | 12/1994 | Pitkin | 623/51 |
| 5,800,569 | 9/1998 | Phillips | 623/53 |
| 5,993,488 | 11/1999 | Phillips | 623/55 |

FOREIGN PATENT DOCUMENTS

| 308671 * | 10/1918 | (DE) | 623/55 |
|---|---|---|---|
| 834884 * | 3/1952 | (DE) | 623/49 |
| 1134045 | 11/1968 | (GB) | 623/55 |
| 2110936 * | 6/1983 | (GB) | 623/49 |
| WO 89/05617 | 6/1989 | (WO) | 623/53 |

OTHER PUBLICATIONS

"Synthesis of a cycloidal mechanism of the prosthetic ankle", M.R. Pitkin, *Prosthetic and Orthotics International*, 1996, 20, 159–171.

* cited by examiner

*Primary Examiner*—Bruce Snow
(74) *Attorney, Agent, or Firm*—Weingarten, Schurgin, Gagnebin & Hayes LLP (57) ABSTRACT An artificial foot and ankle is provided having a keel component, an ankle component, and a central bumper component interposed between the keel component and the ankle component. The ankle component has a lower surface with a radius of curvature greater than the radius of curvature of an upper surface of the keel component in both a sagittal plane and a frontal plane. The curvature of the central bumper component corresponds to the curvature of the keel component. A holding assembly holds the keel component, the ankle component, and the central bumper component together, with the ankle component capable of rolling motion relative to the keel component in both the sagittal plane and the frontal plane. A dorsiflexion stop assembly may also be provided to control the amount of dorsiflexion.

29 Claims, 5 Drawing Sheets

ARTIFICIAL FOOT AND ANKLE

CROSS REFERENCE TO RELATED APPLICATIONS

This application claims priority under 35 U.S.C. §119(e) of U.S. Provisional Application No. 60/126,348, filed Mar. 26, 1999, the disclosure of which is incorporated by reference herein.

STATEMENT REGARDING FEDERALLY SPONSORED RESEARCH OR DEVELOPMENT

The development of this invention was supported by Grant 5R44 AR43290-03 from the National Institutes of Health/National Institute of Arthritis and Musculoskeletal Diseases.

BACKGROUND OF THE INVENTION

Many biomechanical systems or prostheses are known that assist an amputee in walking, running, and performing other types of locomotion. One known type of artificial foot and ankle is disclosed in U.S. Pat. No. 5,376,139, the disclosure of which is incorporated by reference herein. This prosthetic device provides contacting cam rolling surfaces and elastic connections that more closely imitate the forces on the foot during locomotion.

SUMMARY OF THE INVENTION

The present invention relates to an artificial foot and ankle based on the principles of operation of the artificial foot and ankle in the above noted U.S. Pat. No. 5,376,139. The artificial foot and ankle includes a keel component, an ankle component, and a central bumper component interposed between the keel component and the ankle component. The ankle component has a lower surface with a radius of curvature greater than the radius of curvature of an upper surface of the keel component in both a sagittal plane and a frontal plane. The curvature of the central bumper component corresponds to the curvature of the keel component. In this way, the ankle component is capable of a rolling motion over the central bumper component and the keel component.

A holding assembly holds the keel component, the ankle component, and the central bumper component together. The holding assembly comprises a generally U-shaped member disposed along medial and lateral sides and a bottom surface of the keel component and along medial and lateral sides of the central bumper component. A pin extends between upper ends of the U-shaped member and is disposed through an opening in the ankle component, whereby the ankle component is capable of rotation about the pin. The pin may be adjustable on the U-shaped member to provide a desired amount of motion of the foot and ankle.

A dorsiflexion stop assembly may also be provided to control the amount of dorsiflexion. The dorsiflexion stop assembly comprises a strap member extending through corresponding openings in the keel component and the central bumper component and attached to a dorsiflexion rod adjustably mounted at the anterior of the ankle component to provide a tension adjustment of the strap member. A compressible strap bumper may be disposed within a loop of the strap member to provide a gradual dorsiflexion stop.

DESCRIPTION OF THE DRAWINGS

The invention will be more fully understood from the following detailed description taken in conjunction with the accompanying drawings in which.

DETAILED DESCRIPTION OF THE INVENTION

Figure 1:
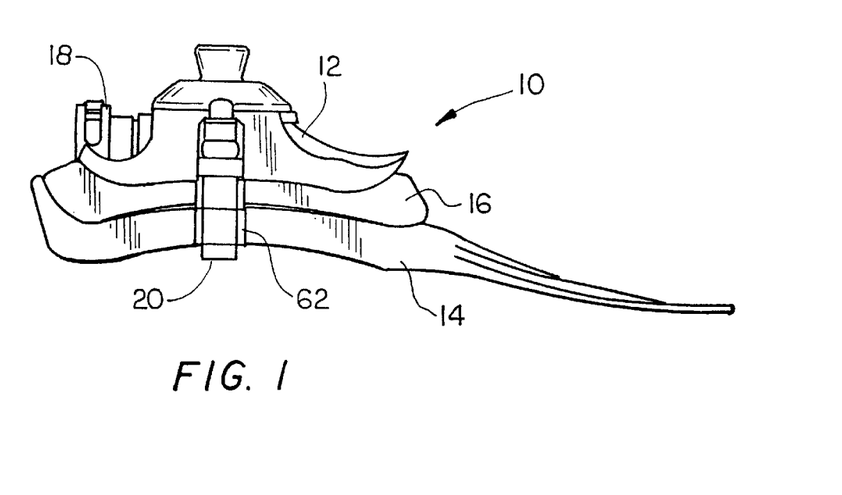
FIG. 1 is a side view of the artificial foot and ankle of the present invention.
Figure 2:
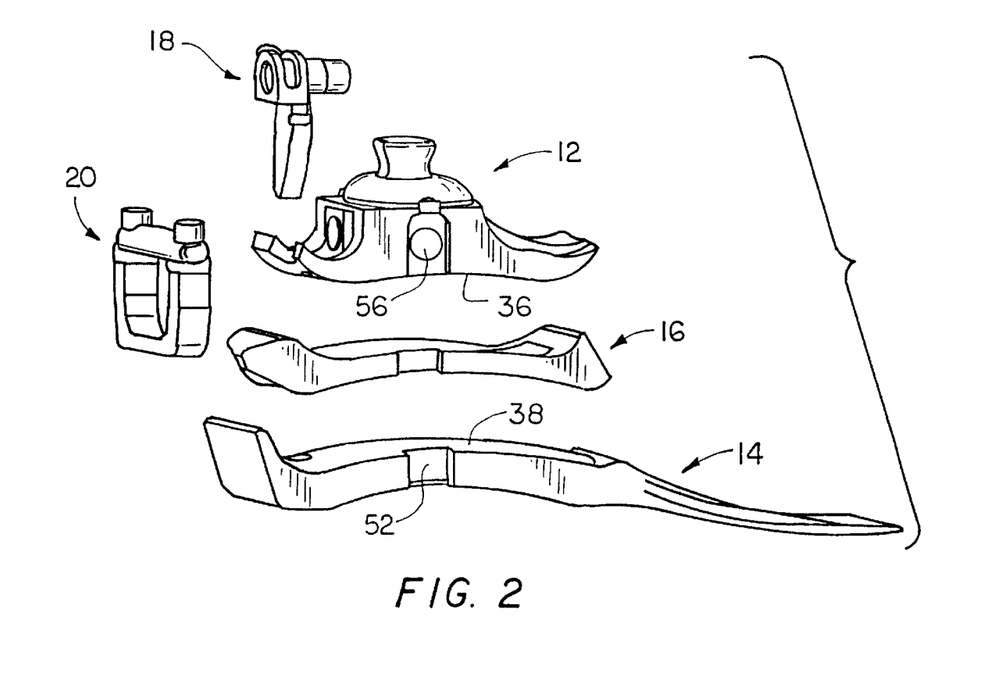
FIG. 2 is an exploded view of the artificial foot and ankle of FIG. 1.

Referring to FIGS. 1 and 2, an artificial foot and ankle assembly 10 of the present invention comprises an ankle component 12, a keel component 14, a central bumper component 16, and a dorsiflexion stop assembly 18. The components are held together by a holding assembly 20.

Figure 3:
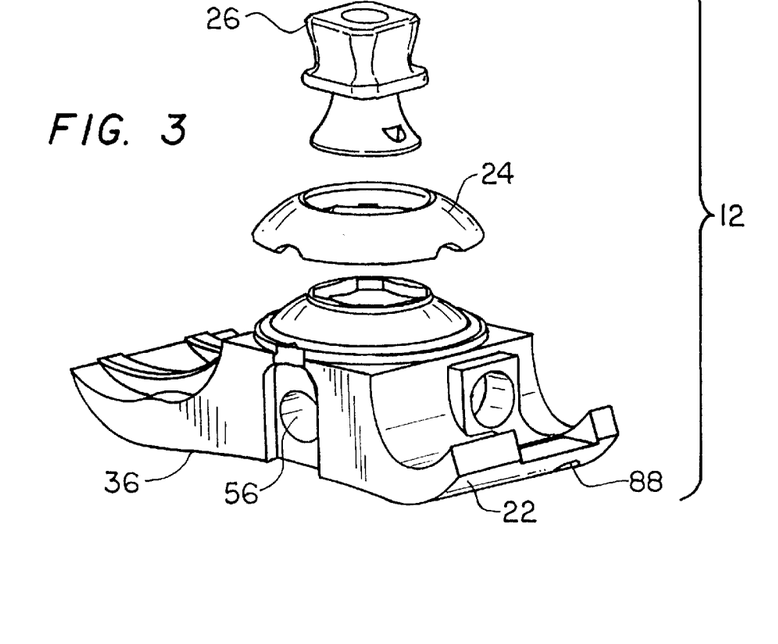
FIG. 3 is an exploded view of an ankle component.

The ankle component 12, shown more fully in FIG. 3, includes a main ankle member 22, a dome 24, and an inverted pyramid 26 molded in for attachment to other components. The ankle component is preferably made from a glass and/or carbon reinforced vinyl ester material. The lay-up of the material provides the required strength.

Figure 4:
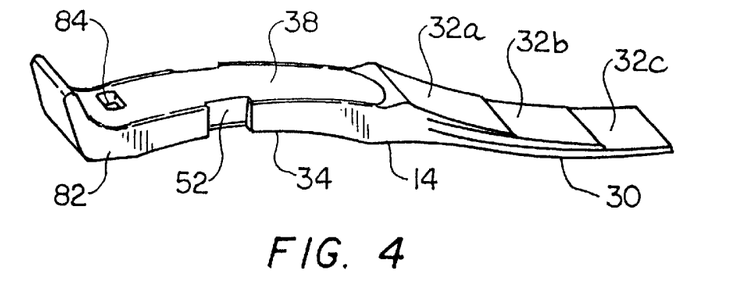
FIG. 4 is an isometric view of a keel component.

Referring to FIG. 4, the keel component 14 is also made from a glass and/or carbon reinforced vinyl ester material. The toe portion 30 of the keel component 14 constitutes a leaf spring design having any suitable number of graduated layers or plates 32a, 32b, 32c (three are shown) to allow for a more responsive forefoot. The particular configuration of the toe portion is determined by the user's parameters and preferences. The keel component also has an arch 34 along its bottom surface to provide the keel component with a fairly uniform thickness and a reduced weight.

The radius of curvature on the bottom surface 36 of the ankle component 12 faces downwardly, and the radius of curvature on the top surface 38 of the keel component 14 faces upwardly, as can be seen in FIG. 2. The magnitude of the radius of the ankle component is greater than the magnitude of the radius of the keel component in both the sagittal and frontal planes.

Figure 5:
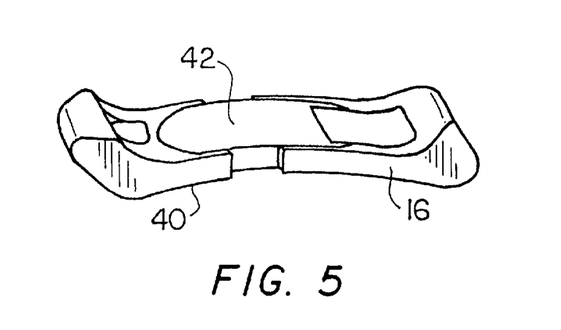
FIG. 5 is an isometric view of a central bumper.
Figure 6:
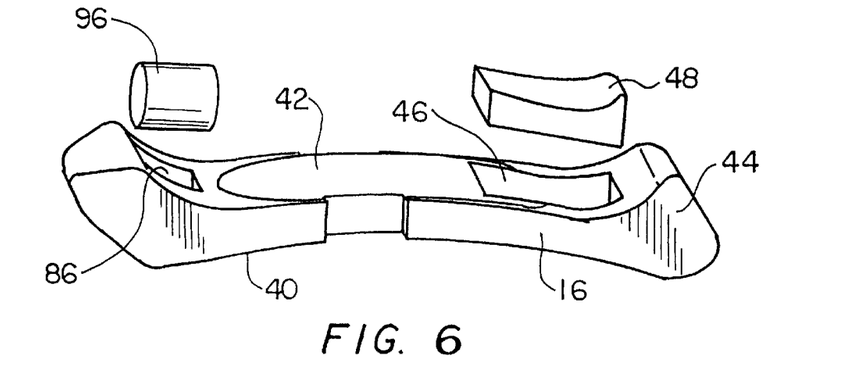
FIG. 6 is an exploded view of the central bumper of FIG. 6.

Referring to FIGS. 5 and 6, the central bumper component 16 is provided between the ankle and keel components 12, 14. The central bumper component is preferably formed from an elastic, polyurethane material, which provides shock absorption and serves to restore the foot to its neutral position after a plantarflexion, dorsiflexion, inversion, or eversion load is applied. The central bumper component preferably has a hardness value between 50A and 90A. The actual hardness is determined by the user's parameters and preferences.

The radius of curvature of the central bumper component is equal to the radius of curvature of the keel component on both the bottom and top surfaces 40, 42 of the bumper. This allows for the ankle component to roll along the top surface 42 of the bumper component. Also, during rolling motion, the surface 36 of the ankle component disengages from the top surface 42 of the bumper component in zones distant from the instant center of contact. The optimal values of the radii of the surfaces 36 and 38 can be determined as known in the art. See Pitkin, M. "Synthesis of cycloidal mechanism of prosthetic ankle," *Prosthetics and Orthotics International*, vol. 20, no. 3 (1996), pp. 159–171.

The anterior portion 44 of the central bumper component 14 may have an optional pocket 46 which allows a separate toe bumper 48 of different hardness to be inserted and interchanged. This allows for additional customization of the forefoot to a patient's parameters and preferences. The toe bumper has a hardness value between 60A and 90A.

Figure 7:
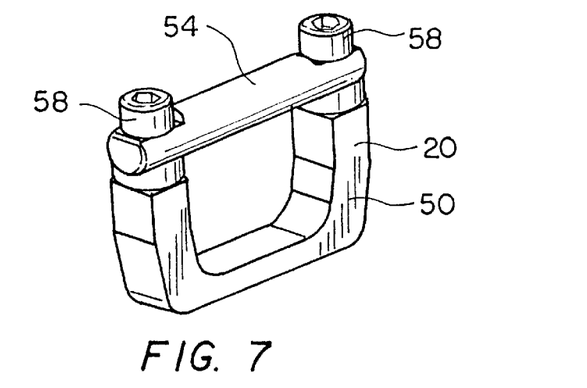
FIG. 7 is an isometric view of a holding assembly.
Figure 8:
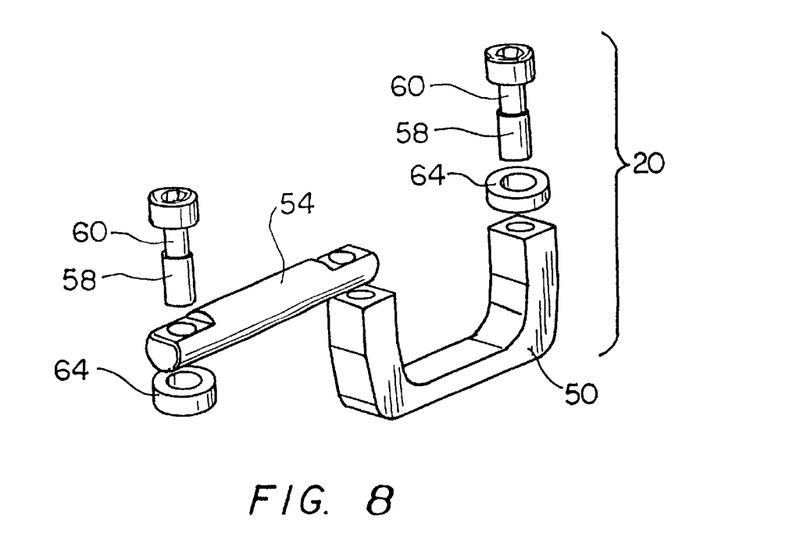
FIG. 8 is an exploded view of the holding assembly of FIG. 7.

The holding assembly, illustrated in FIGS. 7 and 8, holds the ankle, central bumper, and keel components together. In the embodiment shown, the holding assembly includes a U-shaped bracket 50, preferably formed of metal, which fits around the keel component 14 and the central bumper component 16. The keel component has grooves 52 on both the medial and lateral sides through which the bracket passes. The grooves are oversized sufficiently to provide the bracket with limited motion therein. An axial pin 54, preferably made of metal, runs through a hole 56 in the ankle component 12 with its axis in a medial/lateral direction. The hole in the ankle component is oversized sufficiently to allow rotation of the pin 54 within the ankle component. The axial pin is connected to the bracket 50 by two side bolts 58. The axial pin, side bolts, and bracket create a closed loop holding the ankle, central bumper, and keel components together. The holding assembly, however, is not fixed to the keel or the ankle components. This allows for axial rotation of the bracket about the shank, while the ankle component 12 becomes engaged in rolling motion relative to the keel 14 during plantarflexion/dorsiflexion, and inversion/eversion.

The side bolts 58 are shaped similarly to a shoulder bolt. The non-threaded portion 60 of the bolt sits within the axial pin 54. Therefore, the bolt is free to turn within the axial pin. This allows for a method of adjusting ankle motion. By tightening the side bolts, the bracket is drawn tighter against the ankle/bumper/keel assembly, restricting ankle motion. By loosening the side bolts, the ankle motion becomes less restricted.

Referring to FIG. 1, a rubber material 62 is located around the bracket within the grooves of the keel. This material is compressible to allow for axial rotation and creates a force to restore the foot to its neutral position. It also eliminates noise and wear that would occur if the bracket 50 and the keel component 14 were able to come in direct contact.

Around each side bolt 58, between the axial pin 54 and the bracket 50, a circular polyurethane bumper or muffler 64 is used to eliminate noise that would otherwise occur between the bolt and the axial pin. Each muffler creates forces that hold each bolt tightly within the axial pin and the bracket eliminating the rattling noise.

Figure 9:
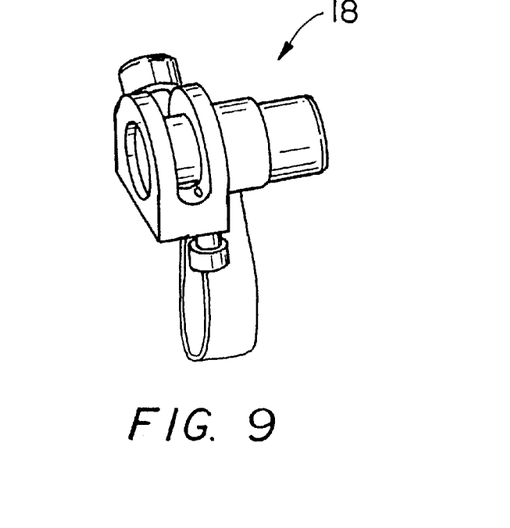
FIG. 9 is an isometric view of a dorsiflexion stop.
Figure 10:
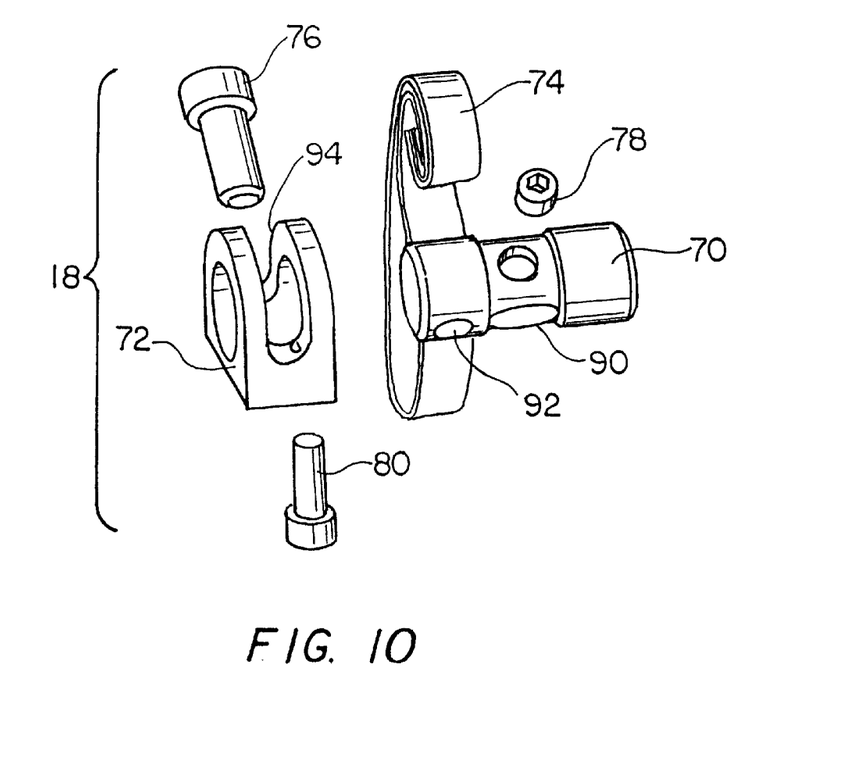
FIG. 10 is an exploded view of the dorsiflexion stop of FIG. 9.

Referring to FIGS. 9 and 10, the dorsiflexion stop assembly 18 is provided to better control the amount of dorsiflexion possible in the foot and ankle assembly. The stop assembly consists of a dorsiflexion rod 70, a dorsiflexion shell 72, a dorsiflexion strap 74, a dorsiflexion stop bolt 76, and an attachment bolt 80. The dorsiflexion strap 74 is preferably made of aromatic polyamide fiber (Kevlar™), Ultra High Molecular Weight Polyethylene Fiber (Spectra™), nylon fiber (Vectran™), or a similar material.

The posterior area 82 in the keel component 14 contains two through holes 84 (see FIG. 4; only one through hole is visible). The area between the holes is rounded on the bottom to create a smooth surface. Each end of the dorsiflexion strap passes through each hole in the keel component so that the strap's midsection passes over the smoothed area between the holes of the keel component. The strap then passes through an open area 86 of the central bumper component 16 and up through a hole 88 in the posterior portion of the ankle component (see FIG. 3). The two ends of the strap are inserted into a slot 90 in the dorsiflexion rod and fastened in place, for example, with a set screw 78. The dorsiflexion rod 70 is then inserted into the dorsiflexion shell 72. By rotating the dorsiflexion rod 70 along its axis, the tension in the dorsiflexion strap 74 may be adjusted.

The dorsiflexion stop bolt 76 is placed through a hole 92 in the dorsiflexion rod 70 and tightened against the dorsiflexion shell 72 to hold the rod in its position after the tension of the strap has been adjusted. The dorsiflexion shell has a slot 94 along its top to allow the bolt 76 to be loosened and rotated along the dorsiflexion rod axis. This provides for adjustment of the dorsiflexion strap tension, thereby controlling the amount of dorsiflexion possible in the foot and ankle assembly.

Referring to FIG. 6, within the central bumper component 16 and between the dorsiflexion strap 74 is a cylindrically shaped bumper or strap bumper 96. As the foot and ankle assembly is dorsiflexed, the dorsiflexion strap 74 tightens on the strap bumper 96. This bumper then provides a more gradual dorsiflexion stop as it compresses. The strap bumper preferably has a hardness value between 50A and 70A. This strap also provides a "safety" in case the holding assembly 20 fails. The strap helps hold the foot assembly together, so that the patient has time to react to the holding assembly failure.

Before the cosmetic finishing is started, a rubber wedge is placed under the heel portion of the keel. This rubber heel wedge provides greater shock absorption. It may be customized to a patient's parameters and preferences. It may also be used to adjust for heel height.

For cosmetics, foam is poured around the keel portion of the foot assembly. A recessed area is provided at the ankle to allow the prosthetist better access to make adjustments. A foam ankle block is then "snapped" into place, for example, using plastic fasteners, to create a cosmetically appealing foot shape.

The motion of the foot and ankle assembly is such that at heel strike the central bumper component 16 compresses, allowing the ankle component 12 to rotate about the axial pin 54 and allowing foot flat by engaging the ankle component 12 in a rolling motion relative to the keel 14. The rubber heel wedge and central bumper component 16 also provide shock absorption. As the gait cycle continues, the ankle component 12 rotates about the axial pin 54, the load applied compresses more of the central bumper component 16, and the holding assembly 20 moves away from the keel component 14 a small amount. This allows free mobility of the ankle component 12 similar to the mobility of an anatomically sound ankle. This mobility allows the keel component 14 to conform to uneven terrain as the ankle component 12 rolls along the top of the central bumper component 16. As the foot goes past mid stance, the dorsiflexion strap 54 gradually tightens as the strap bumper 96 compresses, creating a fixed mobility of the ankle component 12. The body weight is then transferred over the toe portion 30 and the toe plates 32a–c of the keel component 14 to provide stability. At toe off, the plates 32a–c provide energy return, and the bumpers 48, 96 return to their neutral shape, forcing the other components of the foot and ankle assembly to return to their neutral positions.

In an alternative embodiment, the keel component, or just the toe portion of the keel component, may be made using a carbon-epoxy material to provide more energy return in the toe portion. The keel and ankle components may be made from any plastic or any fiber-reinforced plastic.

Figure 11:
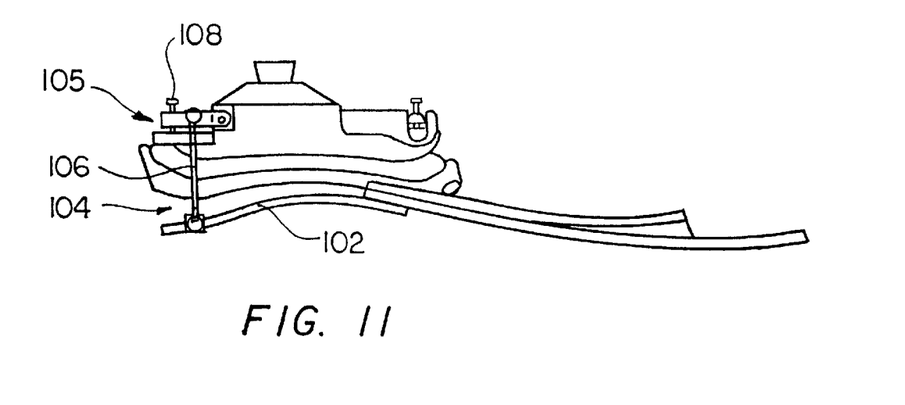
FIG. 11 is a side view of a further embodiment of the present invention.

Additionally, referring to FIG. 11, an alternative holding assembly 105 may be provided. In this embodiment, a heel plate 102 is attached to the keel component and projects posteriorly, creating a gap 104 between the heel plate and the keel component. Steel cables 106 are attached to the heel plate and run up through the central bumper component to attach to the ankle component. At heel strike, the heel plate collapses against the keel component, reducing the tension in the steel cables and allowing the ankle component to rotate relative to the keel, resulting in a dorsiflexion foot motion. To increase the tension in the cable, a bolt 108 located at the attachment point may be turned clockwise, forcing the attachment to move upward. To decrease tension, the bolt may be turned counterclockwise, lowering the attachment piece.

Figure 12:
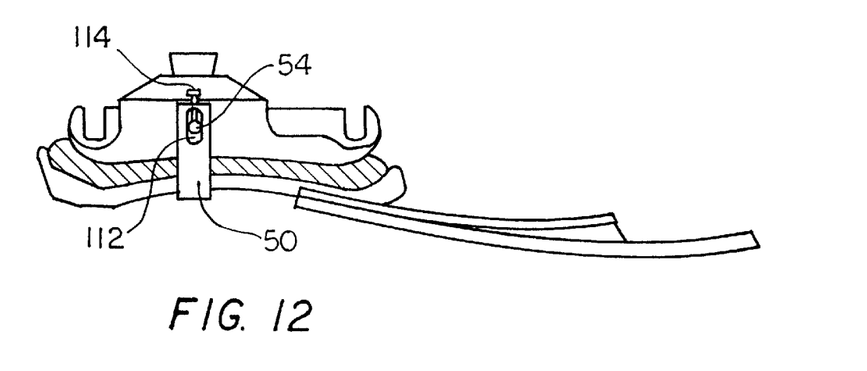
FIG. 12 is a side view of a still further embodiment of the present invention.

In a further embodiment, illustrated in FIG. 12, instead of the axial pin being bolted to the bracket, the pin 54 may fit through slots 112 in the top portion of the bracket 50. A bolt 114 threaded into the top of the bracket on each side may then hold the axial pin from the top. By tightening each bolt, the axial pin drives the ankle component against the central bumper, limiting the ankle motion. Loosening each bolt allows for increased motion.

Other alternative embodiments are contemplated by the present invention. For example, the ankle may have an attachment mechanism other than an inverted pyramid, such as a clamp. The holding assembly may be, for example, a spring or elastic band on each side or encircling the components. One end of the spring may be attached to the keel and the other end to the ankle. The foot may have a split toe for greater inversion/eversion capability.

The invention is not to be limited by what has been particularly shown and described, except as indicated by the appended claims.

What is claimed is:

1. An artificial foot and ankle comprising:
    a keel component having an upper surface, the upper surface having a selected radius of curvature in both a sagittal plane and a frontal plane;
    an ankle component having a lower surface, the lower surface having a selected radius of curvature in both the sagittal plane and the frontal plane;
    a central bumper component interposed between the keel component and the ankle component; and
    a holding assembly holding together the keel component, the ankle component, and the central bumper component;
    wherein the ankle component is configured to disengage from the central bumper component in at least one zone distant from a region of contact pressure during rolling motion.

2. The artificial foot and ankle of claim 1, wherein the holding assembly comprises a closed loop holding the keel component, the ankle component, and the central bumper component with the ankle component capable of rolling motion relative to the keel component in the sagittal plane and the frontal plane and a horizontal plane.

3. The artificial foot and ankle of claim 1, wherein the selected radius of curvature in the sagittal plane of the lower surface of the ankle component is greater than the selected radius of curvature in the sagittal plane of the upper surface of the keel component.

4. The artificial foot and ankle of claim 1, wherein the central bumper component has an upper surface and a lower surface, the upper surface and the lower surface having a radius of curvature corresponding to the radius of curvature of the upper surface of the keel component in both the sagittal plane and the frontal plane.

5. The artificial foot and ankle of claim 1, wherein the holding assembly includes a heel plate attached to the keel component, and cables attached to the heel plate and the ankle component.

6. The artificial foot and ankle of claim 5, wherein the holding assembly includes a tension adjustment mechanism operative to adjust the tension in the cables.

7. The artificial foot and ankle of claim 1, wherein the keel component is formed of a plastic material of a fiber-reinforced plastic material.

8. The artificial foot and ankle of claim 1, wherein the keel component is formed of a glass-reinforced or carbon-reinforced or glass-and-carbon-reinforced vinyl ester material or a carbon-epoxy material.

9. The artificial foot and ankle of claim 1, wherein the keel component includes a toe portion and the toe portion is formed of a carbon-epoxy material.

10. The artificial foot and ankle of claim 1, wherein the keel component includes a toe portion, the toe portion comprising a leaf spring assembly.

11. The artificial foot and ankle of claim 10, wherein the toe portion comprises a plurality of graduated layers.

12. The artificial foot and ankle of claim 1, wherein the keel component further includes an arched bottom surface.

13. The artificial foot and ankle of claim 1, wherein the keel component includes a mid portion having a uniform thickness.

14. The artificial foot and ankle of claim 1, wherein the central bumper component is formed of an elastic material selected to provide shock absorption and a restoring force to return the artificial foot and ankle to a neutral position after application of a load.

15. The artificial foot and ankle of claim 1, wherein the central bumper component includes an anterior portion having a toe bumper pocket formed therein, and a toe bumper is disposed in the toe bumper pocket, the toe bumper having a hardness value different from a hardness value of the central bumper component.

16. The artificial foot and ankle of claim 1, wherein the ankle component is formed of a plastic material or a fiber-reinforced plastic material.

17. The artificial foot and ankle of claim 1, wherein the ankle component is formed of a glass-reinforced or carbon-reinforced or glass-and-carbon-reinforced vinyl ester material.

18. The artificial foot and ankle of claim 1, wherein the ankle component further includes an attachment element extending from an upper surface.

19. The artificial foot and ankle of claim 1, further comprising a dorsiflexion stop assembly disposed to control dorsiflexion of the artificial foot and ankle.

20. The artificial foot and ankle of claim 19, wherein the dorsiflexion stop assembly comprises a strap member extending through corresponding openings in the keel component and the central bumper component and attached to a dorsiflexion rod adjustably mounted at the posterior of the ankle component to provide a tension adjustment of the strap member.

21. The artificial foot and ankle of claim 20, further comprising a compressible strap bumper disposed within a loop of the strap member to provide a gradual dorsiflexion stop.

22. An artificial foot and ankle comprising:
- a keel component having an upper surface, the upper surface having a selected radius of curvature in both a sagittal plane and a frontal plane;
- an ankle component having a lower surface, the lower surface having a selected radius of curvature in both the sagittal plane and the frontal plane, the ankle component further including a hole therethrough in a direction lying in the frontal plane;
- a central bumper component interposed between the keel component and the ankle component; and
- a holding assembly holding together the keel component, the ankle component, and the central bumper component, the holding assembly further including a pin disposed in the hole through the ankle component to provide rotation of the ankle component about the pin.

23. An artificial foot and ankle comprising:
- a keel component having an upper surface, the upper surface having a selected radius of curvature in both a sagittal plane and a frontal plane;
- an ankle component having a lower surface, the lower surface having a selected radius of curvature in both the sagittal plane and the frontal plane;
- a central bumper component interposed between the keel component and the ankle component; and
- a holding assembly holding together the keel component, the ankle component, and the central bumper component, the holding assembly comprising:
  - a generally U-shaped member disposed along medial and lateral sides and a bottom surface of the keel component and along medial and lateral sides of the central bumper component, and
  - a pin extending between upper ends of the U-shaped member and disposed through an opening in the ankle component, the ankle component capable of axial rotation about the pin.

24. The artificial foot and ankle of claim 23, wherein the U-shaped member rests within grooved regions along the medial and lateral sides of the keel component, and the grooved regions are sized to allow selected motion of the U-shaped member.

25. The artificial foot and ankle of claim 23, wherein the pin is adjustably connected to ends of the U-shaped member.

26. The artificial foot and ankle of claim 23, wherein the pin is connected to ends of the U-shaped member with adjustable bolts.

27. The artificial foot and ankle of claim 23, wherein the holding assembly further includes a muffler between each of the ends of the U-shaped member and the pin.

28. The artificial foot and ankle of claim 23, wherein the pin is adjustably disposed through slots at upper ends of the U-shaped member.

29. The artificial foot and ankle of claim 23, further comprising a compressible element disposed in the medial and lateral grooved regions in the keel component between the keel component and the U-shaped member.

* * * * *

UNITED STATES PATENT AND TRADEMARK OFFICE
CERTIFICATE OF CORRECTION

PATENT NO.     : 6,290,730 B1
DATED          : September 18, 2001
INVENTOR(S)    : Mark R. Pitkin et al.

Page 1 of 1

It is certified that error appears in the above-identified patent and that said Letters Patent is hereby corrected as shown below:

Column 1,
Line 14, please insert the following sentence: -- The government has certain rights in the invention. --

Signed and Sealed this

Thirtieth Day of April, 2002

Attest:

JAMES E. ROGAN
Attesting Officer     Director of the United States Patent and Trademark Office